US006440112B1

(12) United States Patent
Glaug et al.

(10) Patent No.: US 6,440,112 B1
(45) Date of Patent: Aug. 27, 2002

(54) EASY TO MANUFACTURE INCONTINENT PAD

(75) Inventors: Frank S. Glaug, Chester Springs; Jean A. Serafino, Clifton Heights, both of PA (US)

(73) Assignee: Tyco Healthcare Retail Services AG (CH)

( * ) Notice: Subject to any disclaimer, the term of this patent is extended or adjusted under 35 U.S.C. 154(b) by 0 days.

(21) Appl. No.: 09/472,394

(22) Filed: Dec. 27, 1999

(51) Int. Cl.[7] .................................................. A61F 13/15
(52) U.S. Cl. .................... 604/385.01; 604/387; 604/389
(58) Field of Search ....................... 604/385.01; 156/227

(56) References Cited

U.S. PATENT DOCUMENTS

| | | | | |
|---|---|---|---|---|
| 4,770,657 A | * | 9/1988 | Ellis ........................... | 604/385 |
| 5,520,673 A | * | 5/1996 | Yarbrough ................... | 604/378 |
| 5,653,842 A | * | 8/1997 | Kuen ........................... | 156/227 |
| 5,704,928 A | * | 1/1998 | Morita ................... | 604/385.01 |
| 5,817,086 A | * | 10/1998 | Kling ..................... | 604/385.02 |
| 5,876,390 A | * | 3/1999 | Hall ....................... | 604/385.02 |
| 5,947,948 A | * | 9/1999 | Roe ....................... | 604/385.02 |

* cited by examiner

Primary Examiner—A Vanatta
Assistant Examiner—Angela J. Grayson

(74) Attorney, Agent, or Firm—Caesar, Rivise, Bernstein, Cohen & Poktilow, Ltd.

(57) ABSTRACT

A disposable absorbent pad arranged to be worn in an undergarment to trap and collect urine. The pad has a moisture pervious, e.g., fibrous, top-sheet, a fluid acquisition layer, an absorbent core, and a moisture-impervious, e.g., polymeric film, back-sheet. The back-sheet is formed of a fluid impervious material, e.g., a polymeric film. The fluid acquisition layer is disposed over the core and both it and the core are interposed between the top-sheet and the back-sheet. The back-sheet has an opposed pair of arcuate edge portions and an opposed pair of linear side edges. The top-sheet has an opposed pair of arcuate edges and an opposed pair of side portions. Each of the side portions of the top-sheet merges with the remainder of the top-sheet along a respective fold line and each is of a generally trapezoidal shape. The arcuate edges of the top-sheet are disposed over respective ones the arcuate edges of the back-sheet. The top-sheet and back-sheet are secured together. The side portions of the top-sheet are folded along respective ones of the fold line around respective linear side edges of the back-sheet and are adhesively secured thereto. Plural elastic strands are adhesively secured in place along the fold lines of the top-sheet to form elasticized side shields. An adhesive stripe is located on the back-sheet for mounting the pad in a garment. The adhesive stripe is covered by a removable liner strip.

16 Claims, 4 Drawing Sheets

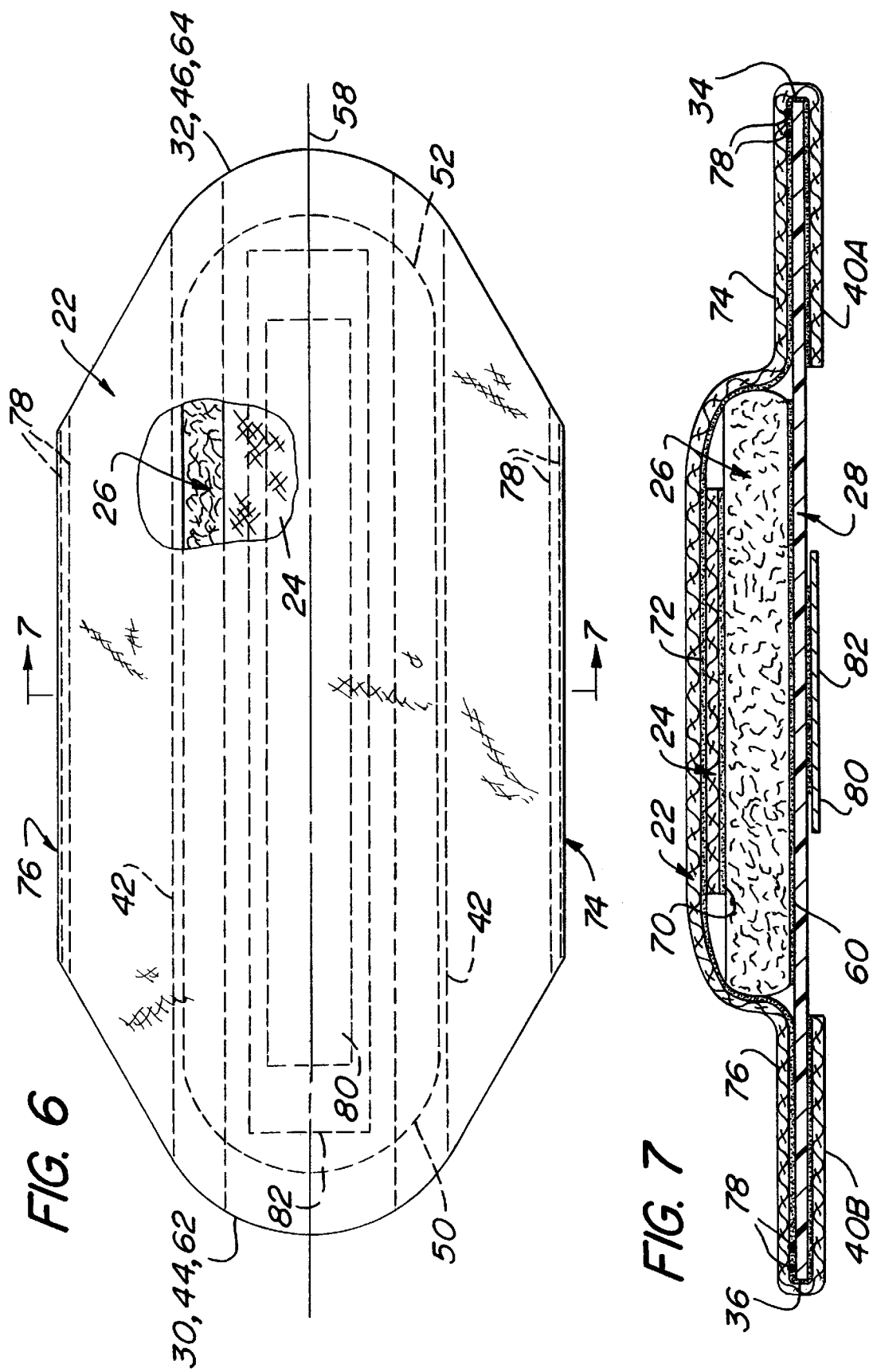

EASY TO MANUFACTURE INCONTINENT PAD

FIELD OF THE INVENTION

This invention relates generally to disposable absorbent incontinency articles, and more specifically to disposable absorbent pads which are arranged to be worn and concealed under clothing and which are easy to manufacture.

BACKGROUND OF THE INVENTION

As populations continue to increase in longevity, incontinence, a problem of age presents a need for fluid control in undergarments. In particular, adult incontinence represents a transition from underwear to the use of some type of absorbent article to be added to the underwear or to completely replace it. For moderate-to-heavy incontinence needs a variety of disposable diaper designs are commercially available. However, such diapers have various deficiencies. For example, many of them, particularly high capacity diapers, are thick and bulky, thus rendering concealment difficult. Moreover many of such prior art absorbent articles are complex in construction. See for example, U.S. Pat. No. 5,520,673 (Yarbrough et al.), U.S. Pat. No. 5,876,390 (Hall et al.), U.S. Pat. No. 5,817,086 (Kling), and U.S. Pat. No. 5,947,848 (Roe et al.).

A more recent development in the field of adult incontinent products is the three dimensionally shaped pad. Such pads are typically somewhat curved elongated members arranged to be worn within an undergarment at the crotch and immediately between the wearer's legs. The pads typically consist of a polymeric film barrier or outer layer, a non-woven fibrous inner layer with an absorbent core interposed between the outer layer and inner layer. A fluid acquisition layer to facilitate the transfer of urine from the inner layer into the core is commonly provided between the inner layer and the core.

Leakage of urine laterally has been a problem with incontinent pads, even with body-shaped pads. Thus, it is a common practice to make use of elasticized edges along those portions of the sides of the pad which are located between the wearer's legs. See for example U.S. Pat. No. 4,770,657 (Ellis et al.).

In the interests of comfort and to prevent lateral urine leakage some prior art elasticized incontinent pads have made use of a pair of "side shields" formed of a fibrous material with elastic threads therein extending along the linear marginal edges of the pad. These elasticized side shields serve to prevent the egress of urine laterally out of the pad. Moreover, the side shields extend over the outer surface of the polymeric film barrier along the marginal side edges of the pad to provide a cloth-like feel on the skin where they engage the wearer. One such pad is presently being marketed by Kimberley Clark Company under the trademark POISE.

While the prior art pads are generally suitable for their intended purposes, they never the less leave something to be desired from one or more of the standpoints of good fit within an undergarment, concealability, resistance to movement or migration, comfort, effectiveness in preventing urine leakage, simplicity of construction and ease of manufacture. A need thus exists in the prior art for adult incontinence pads which addresses drawbacks of the prior art.

OBJECTS OF THE INVENTION

Accordingly, it is a general object of this invention to provide a disposable absorbent pad that addresses the needs of the prior art.

It is another object of this invention to provide a disposable adult incontinent pad that is simple in construction.

It is another object of this invention to provide a disposable adult incontinent pad that is easy to manufacture.

It is another object of this invention to provide a disposable adult incontinent pad that is comfortable.

It is another object of this invention to provide a disposable adult incontinent pad that is easy to conceal within an undergarment.

It is another object of this invention to provide a disposable adult incontinent pad that is resistant to lateral leakage.

SUMMARY OF THE INVENTION

A disposable absorbent article, e.g., an absorbent pad, arranged to be worn under clothing by a person to trap and collect urine. The pad is a flexible member which when flattened is of a generally flat oval shape and basically comprises a top-sheet, a fluid acquisition layer, an absorbent core, and a back sheet. The back sheet is formed of a fluid impervious material, e.g., a polymeric film. The top-sheet is formed of a fluid pervious material, e.g., a fibrous material. The fluid acquisition layer of the pad is interposed between the core and the top-sheet, and the core is interposed between the back sheet and the fluid acquisition layer.

The back sheet has an opposed pair of arcuate end portions and an opposed pair of linear side edges. Each of the arcuate end portions of the back sheet terminate in an arcuate edge. The top-sheet also has an opposed pair of arcuate end portions and an opposed pair of linear side portions. Each of the arcuate end portions of the top-sheet terminate in an arcuate edge, and each of the side portions of the top-sheet terminating in a side edge. The arcuate end portions of the top-sheet are disposed over and secured to respective ones the arcuate end portions of the back sheet. Each of the side portions of the top-sheet are of the same shape, e.g., a generally trapezoidal shape, and merge with the remainder of the top-sheet along respective fold lines. The side portions of the top-sheet are folded along respective ones of the fold line around respective linear side edges of the back sheet and are adhesively secured thereto to produce a pair of side shields.

In accordance with one preferred embodiment of the invention the generally linear sides of the pad are elasticized, e.g., plural elastic strands are adhesively secured in place along the fold lines of the top-sheet. In addition an adhesive stripe is located on the back sheet for mounting the pad in a garment. The adhesive stripe is initially covered by a removable liner sheet until it is ready for use.

DESCRIPTION OF THE DRAWING

FIG. 6 is an enlarged plan view of the pad of FIG. 1 laid flat and as viewed from the top-sheet side of the pad, with portions of the pad broken away;

FIG. 7 is an enlarged sectional view taken along line 7—7 of FIG. 6; and

DETAILED DESCRIPTION OF THE PREFERRED EMBODIMENT

Figure 1:
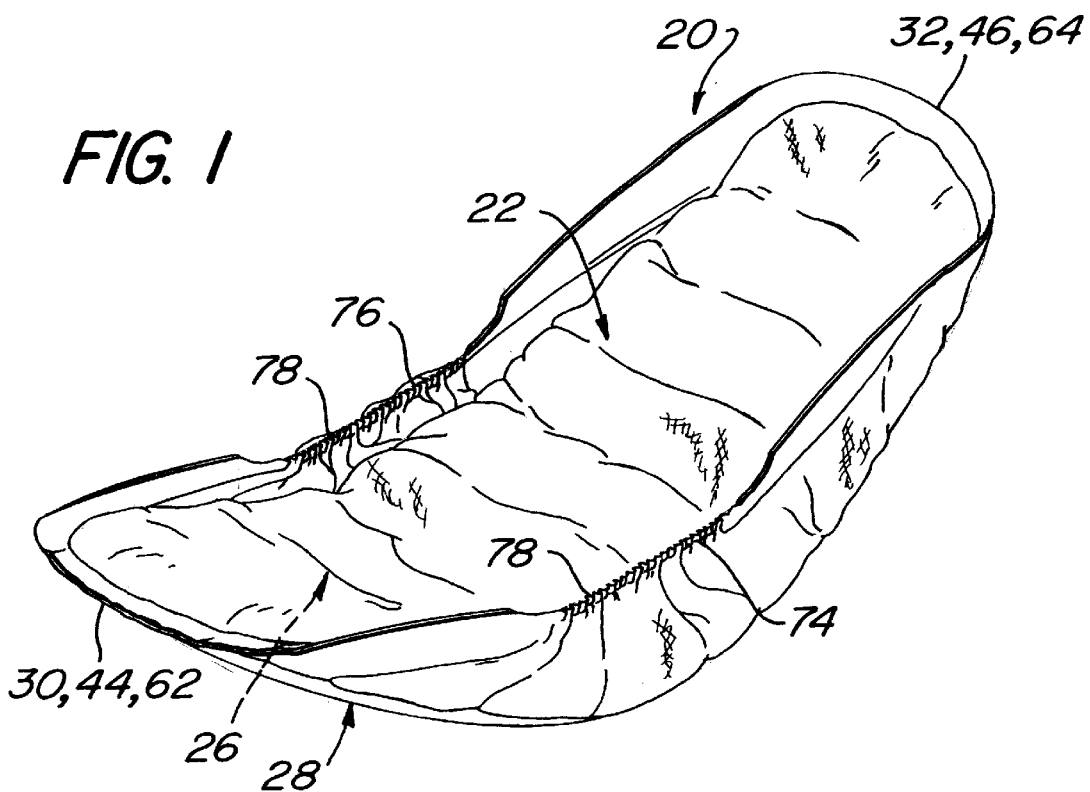
FIG. 1 is an isometric view of a urinary incontinence pad constructed in accordance with this invention.

Referring now to the various figures of the drawing wherein like reference characters refer to like parts, there is shown in FIG. 1 a disposable absorbent article 20 constructed in accordance with one embodiment of this invention. The article 20 of FIG. 1 is in the form of an adult incontinent pad. It should be pointed out that as used herein the term "disposable" means that article is designed to be used until soiled, either by urination or otherwise, and then discarded, rather than being washed and used again.

Figure 4:
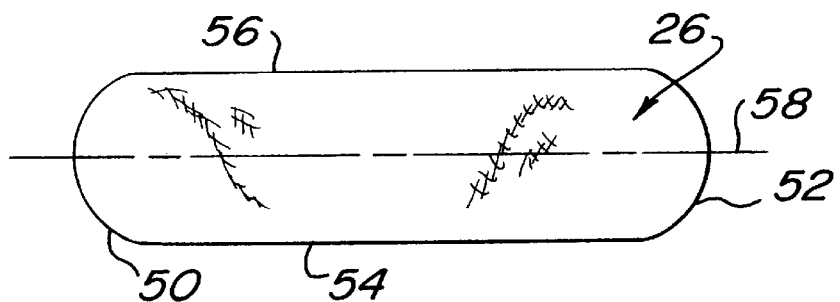
FIG. 4 is a plan view, like that of FIGS. 2 and 3, but showing the core of the pad of FIG. 1.
Figure 5:
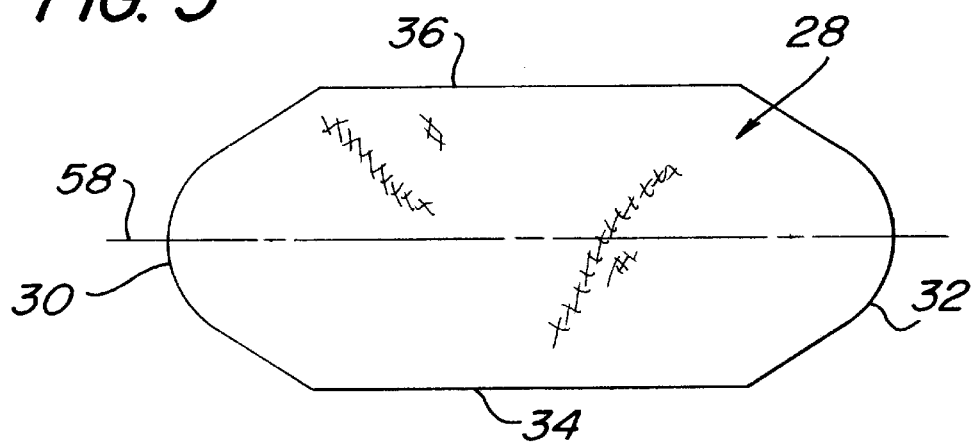
FIG. 5 is a plan view, like that of FIGS. 2–4, but showing the back-sheet of the pad of FIG. 1.

The pad 20 basically comprises a body-side liner or top-sheet 22 (FIG. 2), a fluid acquisition layer 24 (FIG. 3), a liquid absorbent structure or core 26 (FIG. 4), and an outer cover or back-sheet 28 (FIG. 5). The top-sheet 22 is arranged to face toward the body of the wearer, when the pad is in place, with the back-sheet 28 facing away from the wearer. The top-sheet or cover-stock 22 is superimposed over the back-sheet, with the absorbent core 26 interposed therebetween. The top-sheet, as will be described later, is formed of a liquid pervious material to enable liquid, e.g., urine, to readily pass therethrough into the interior of the pad for ultimate absorption and retention by the core 26. The fluid-acquisition layer 24 is disposed on top of the core 26 and under the top-sheet 22 and serves to facilitate the passage of urine into the core for absorption.

As should be appreciated from the discussion to follow when the pad 20 is in place mounted within an undergarment (not shown), the pad will be centered between the legs of the wearer in the wearer's crotch region so that the pad's core can absorb and retain any urine accidentally excreted by the wearer. As is conventional the back sheet is formed of a moisture impervious material to prevent the leakage of urine therethrough. Moreover, as best seen in FIG. 1, the pad includes a pair of elasticized side shields 74 and 76 (to be described later) to prevent the egress of urine from the pad along the sides of the pad.

Turning now to FIG. 5, it can be seen that the back-sheet 28 is a generally flat-oval shaped planar member having an arcuate top end edge 30, an arcuate bottom end edge 32, and a pair of opposed linear side edges 34 and 36. The back-sheet 28 is preferably formed, e.g., die cut, from a sheet of a moisture impervious material, such as a polymeric film. One particularly suitable film is 1.1 mil polyethylene film designated as #XP3454A from Huntsman Packaging of Salt Lake City, Utah. The back-sheet 28 can also be made of other suitable moisture impervious materials, e.g., polypropylene films, co-extruded films (polyethylene and ethylene vinyl acetate), co-polymer films (polyethylene/polypropylene), and polylaminates (polypropylene non-woven and polyethylene film). Still another example is a film made of a "breathable' microporous polyethylene. Suitable breathable films are available from Exxon Chemical Company, Buffalo Grove, Ill. This material allows water vapor to pass through it over time, while being impervious to liquid water. The water vapor transmission rate may range from 200–3000 grams per square meter per 24-hour period.

Figure 2:
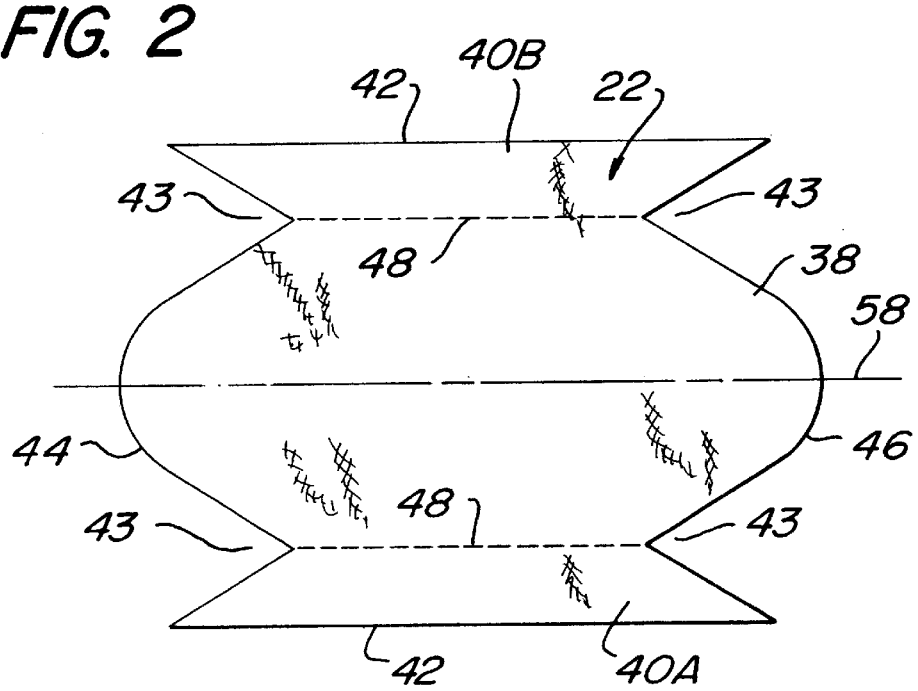
FIG. 2 is a reduced plan view of the top-sheet making up the pad of FIG. 1.

The top-sheet 22 is best seen in FIG. 2 and is also a planar member die cut from any suitable material. Unlike the back-sheet 28 it has a central portion 38 and a pair of side portions or sections 40A and 40B. As mentioned earlier in order to enable urine to quickly and efficiently pass through the top-sheet 22, it is preferably formed of a liquid permeable material. In particular, the top-sheet may be selected from a variety of textile-like films and fabrics. Suitable fabrics include non-woven materials that are pervious to liquid, soft and pliable. Preferred non-woven materials include spun-bonded polypropylene; spunbonded polyethylene; thermally bonded webs of staple fibers preferably polypropylene or sheath/core bi-component fibers having a core of polyester or polypropylene and a sheath of polyethylene. To enhance the fluid control properties of the aforementioned liners, surfactants or wetting agents typified by Triton X-100 and Triton X-102 available from Rohm & Haas Company of Philadelphia, Pa. may be applied to the fluid receiving zones of the liner. If desired, the top-sheet 22 may be formed of a liquid impermeable material, but having a multitude of small apertures or pores extending therethrough so as to make the material liquid permeable.

The top-sheet 22 includes a pair of side edges 42, a top edge 44 and a bottom edge 46. The top edge 44 and bottom edge 46 are each die cut with two deep notches 43 to form a panel having the heretofore identified central portion or section 38 and the pair of side portions or sections 40A and 40B. The central section 38 of the top-sheet 22 is of the same shape and size as the back-sheet 28, namely, a flat oval. In particular, the central portion 38 of the top-sheet 22 includes an arcuate top portion terminating in an arcuate edge 44, and an arcuate bottom portion terminating in an arcuate edge 46. The arcuate edges 44 and 46 of the top-sheet are identical to the edges 30 and 32, respectively, of the back-sheet 28. Each of the side sections 40A and 40B of the top-sheet is of a generally trapezoidal shape having a linear marginal edge 42 and merges with the central section 38 of the top-sheet 22 in respective fold lines 48 (shown by the broken lines in FIG. 2). The side sections 40A and 40B are folded around and secured to the respective linear marginal edges 34 and 36 of the outer surface of the back-sheet 28 along the fold lines 48 to form respective side shields 74 and 76 (to be described later). As will also be described later, the side shields have linear edges and are elasticized along their length to enable the pad to naturally assume a three-dimensional, cup-shape to thereby basically conform to the wearer's anatomy when the pad is mounted and worn within an undergarment.

As best seen in FIG. 4 the core 26 is an elongated generally planar member which is die cut from a sheet or web of material to form a panel having a pair of arcuate ends 50 and 52, and a pair of opposed linear side edges 54 and 56. The core 26 is located in the pad 20 centered along the central longitudinal axis 58 (i.e., the "machine" direction) of the back-sheet 28 and is secured in place on the back-sheet's inner surface with any suitable adhesive, e.g., a construction adhesive 60 (shown by the broken lines in FIG. 7). One particularly suitable adhesive 60 is that sold under the designation Cycloflex adhesive by National Starch and Chemical of Bridgewater, N.J.

The absorbent core 26 can be made up of any suitable liquid absorbent material, as well as combinations of different types of absorbent material(s). For example, in the exemplary preferred embodiment, the core is formed of a mixture of pulp fluff and a super-absorbent-polymer (SAP). The core may be wrapped in a liquid permeable tissue wrap (not shown). Examples of SAP include polyacrylamides, polyvinyl alcohol, polyacrylates, various grafted starches, and the like. A desired super absorbent material is a cross-linked polysodium acrylate, which can be purchased from Chemdal Corporation, Palatine, Ill., under the trademark ASAP #2102. The super absorbent materials can be in various geometric forms, such as various shaped particles, fibers, foams, and layers. The fluff and SAP are present in a ratio of about 30%–40% SAP and 60%–70% fluff, and have a core density range of about 0.15 to 0.19 grams per cubic centimeter. For example, one type of pad (e.g., an "ultra" absorbent type) may contain 6.5 gms SAP and 13 gms pulp or fluff with a core density of approximately 0.17 gms/cc, while an even more absorbent type (e.g., an "ultra plus" absorbent type) may contain 8.5 gms SAP and 15 gms pulp with the same core density.

While the core 26 is shown as being a single, integral absorbent structure or panel, it can comprise a plurality of individual separate absorbent structures and/or absorbent materials that are operably assembled together. It can also consist of air-laid non-woven web that contains super-absorbent particles and/or super-absorbent fibers, polymeric binder and cellulose pulp fibers. The amount of each absorbent material and SAP/fluff ratio depends on the size of the pad and the construction of the liquid acquisition or transfer layer 24.

Figure 3:
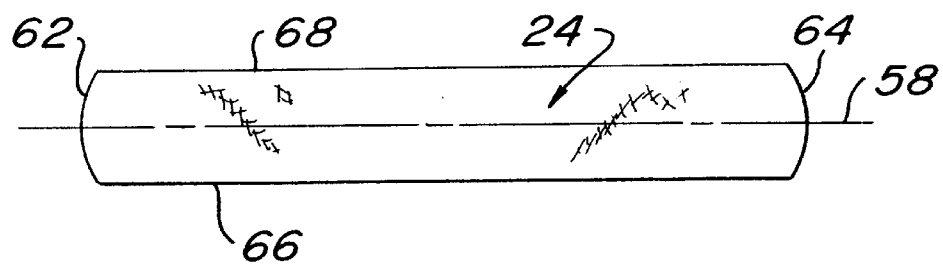
FIG. 3 is a plan view, like that of FIG. 2, but showing the fluid acquisition layer of the pad of FIG. 1.

As is conventional, the fluid acquisition layer 24 serves to manage, transport and/or direct high volumes and high flow rates of urine received from the top-sheet 22 into the absorbent core 26 at a rate that the core 26 can handle, despite multiple insults of urine. As best seen in FIG. 3 the fluid acquisition layer 24 is also an elongated generally planar member die cut from any suitable material to have a pair of arcuate ends 62 and 64 and a pair of opposed linear side edges 66 and 68. The length of the fluid acquisition layer is the same as the length of the central portion 38 of the top-sheet 22 and the length of the back sheet 28. Moreover, the radius of curvature of the ends 62 and 64 is the same as that of the ends 30 and 32 of the back-sheet 28 and the ends 44 and 46 of the top-sheet 22. If desired, the fluid-acquisition layer 24 may be in the form of a rectangle of the same width as just described, but having an abbreviated length which is centered longitudinally and transversely in the pad, with the length of the fluid acquisition layer approximately equal to the length of the linear sides of the pad.

In a preferred exemplary embodiment of this invention the fluid acquisition layer 24 is made up of 50 gms/sq. meter of "surfactant treated" Thermal Bond Polypropylene #6700 from PGI Nonwovens of Landisville, N.J. Alternatively it may comprise a lamination of an apertured, three dimensional polymeric film layer and a non-woven or fibrous layer, such as those disclosed and claimed in copending U.S. patent application Ser. No. 09/439,793, filed on Nov. 12, 1999, entitled Absorbent Article with Improved Fluid Acquisition System, which is assigned to the same assignee as this invention and whose disclosure is incorporated by reference herein.

The fluid acquisition layer 24 is disposed on top of the core 26, is centered along the central longitudinal axis 58 of the back-sheet 28 and is secured in place on the core via a suitable construction or hydrophilic adhesive 70, e.g., the heretofore identified Cycloflex adhesive, and which is shown by the broken lines in FIG. 7.

As mentioned earlier and best seen in FIGS. 6 and 7 the core 26 is disposed on the inner surface of the back-sheet 28 along the longitudinal axis 58 and is secured in place by the adhesive 60. The fluid acquisition layer 24 is disposed on the core 26, centered over the central longitudinal axis 58 and secured in place on the core by the adhesive 70. The top-sheet 22 is in turn joined to the back-sheet 28 utilizing any suitable adhesive 72 (e.g., a construction adhesive or hydrophillic adhesive, such as the aforementioned Cycloflex adhesive) and shown by the broken lines in FIG. 7. The adhesive 72 is preferably applied over the entire inner surface of the top-sheet 22 for reasons to be appreciated from the discussion to follow. However, the adhesive 72 can be applied in any manner such as by spraying, slot-coat extrusion, printing, or the like. Moreover, the applied adhesive 72 can be in any desired configuration or design, such as continuous or discontinuous beads, continuous or discontinuous swirls, meltblown patterns, spray patterns, or the like. Alternatively, the joining of layers and structures can be accomplished by heat sealing, ultrasonic bonding, or the like.

As mentioned earlier each of the side sections 40 and 42 of the top-sheet 22 is folded around a respective one of the linear side edges of the back-sheet 28 to form an associated side shield. In particular, the side section 40A of the top-sheet 22 is folded along its associated fold line 48 so that it extends over the marginal side edge 34 of the back-sheet 28. The section 40A is secured in place by the adhesive 72 on the underside of the top-sheet to form a side shield 74 (FIG. 1) on one side of the pad 20. In a similar manner, the side section 40B of the top-sheet 22 is folded along its associated fold line 48 so that it extends over the marginal side edge 36 of the back-sheet 28 and is secured in place by the adhesive 72 on the underside of the top-sheet 22 to form a side shield 76 (FIG. 1) on the opposite side of the pad.

As also mentioned earlier each of the side shields 74 and 76 is elasticized. In particular, each lateral side edge of the pad 20 is elasticized by means of two pairs of longitudinally extending elastic threads or strands 78, e.g., LYCRA 740 decitex of E.I. DuPont DeNemours & Co., Wilmington, Del. One pair of the strands 78 is disposed between the top-sheet 22 and marginal edge of the back-sheet 28 where the top-sheet 22 is folded along its fold line 48 to form the marginal edge of the side shield 74. The other pair of strands 78 is similarly located between the top-sheet 22 and marginal edge of the back-sheet 28 where the top-sheet is folded to form the marginal edge of the side shield 76. The strands 78 may be obtained from E.I. DuPont de Nemours and Company, Wilmington, Del., and are placed under tension when held in place by the adhesive 72. Other arrangements can be used to elasticize the linear sides of the center portion of the pad.

With the center portion of the pad, i.e., the portion along the linear side shields 74 and 76, being elasticized and under tension, the pad 20 naturally assumes a three dimensional, generally cup-shaped configuration like shown in FIG. 1. In particular, the pad 20 curves from one arcuate end to the other, with the side shields 74 and 76 forming upstanding flanges on either side of the pad. This configuration conforms generally to the crotch of a person (male or female), so that the pad 20 can be readily mounted and concealed within any undergarment to trap and contain any urine which should be inadvertently excreted by the wearer.

Figure 8:
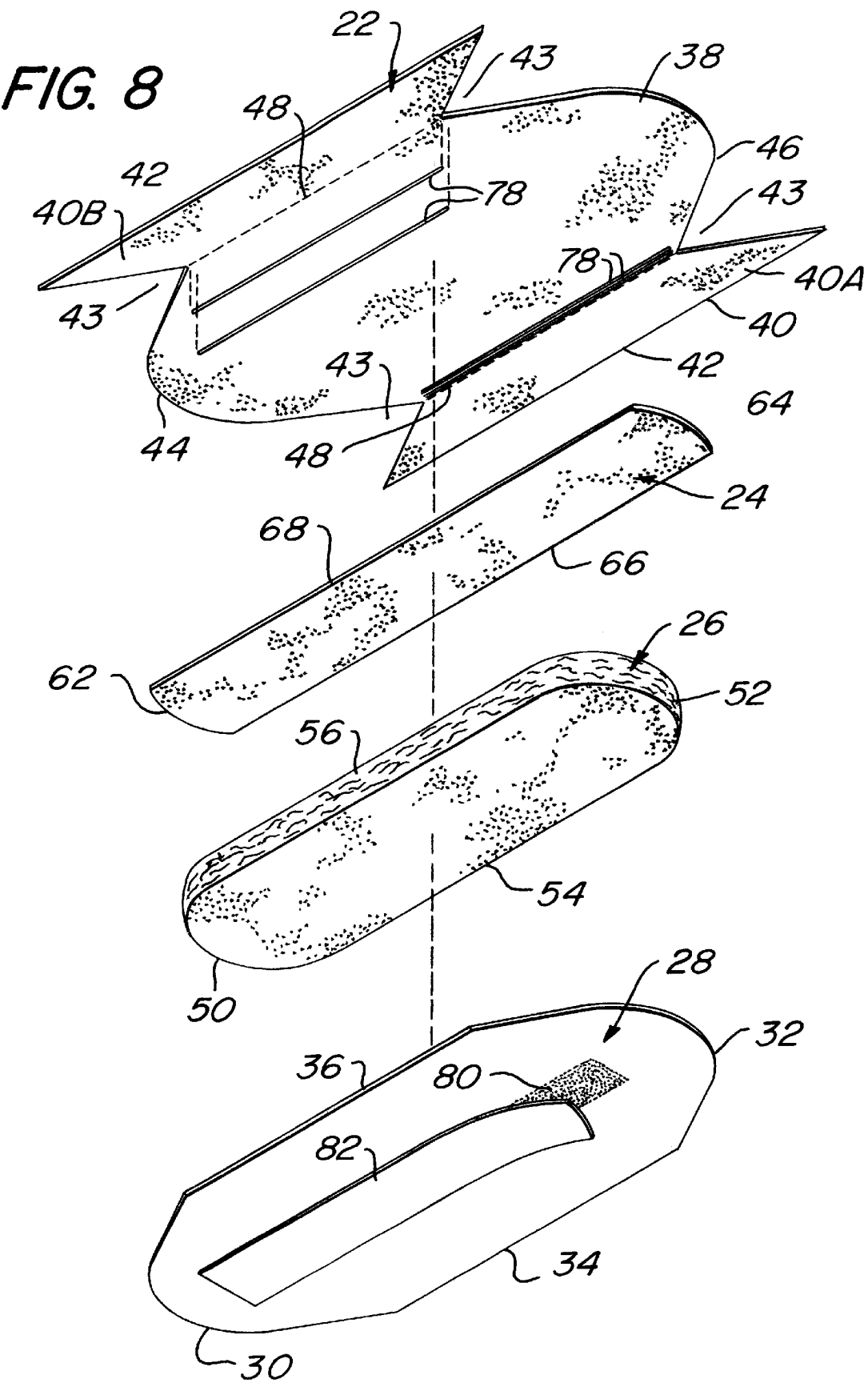
FIG. 8 is an exploded isometric view of the pad of FIG. 1.

In order to hold the pad 20 in place within the wearer's undergarment, the pad includes an elongated stripe 80 of adhesive on the outer surface of the back-sheet 28 extending along the longitudinal central axis 58 of the pad for a major portion of the length of the pad 20 as shown in FIGS. 6–8 . Any suitable positioning adhesive 80 can be used for the stripe 80, such as a pressure sensitive hot melt adhesive. One particularly suitable material for the adhesive 80 is designated as #34-5598, available from National Starch and Chemical of Bridgewater, N.J. In order to protect the adhesive stripe 80 from degradation or being soiled by debris, an elongated release strip 82 (e.g., a release paper) is releasably secured over the stripe 80 as shown in FIGS. 6–8. The release strip 82 can be formed of any suitable adhesive protective, yet easy to release, material. One particularly suitable material for the adhesive release strip 82 is designated as #11636, available from Tekkote of Leonia, N.J.

As will be appreciated by those skilled in the art when the pad 20 is in place within the undergarment and between the wearer's legs, the portions of the outer surface of the pad 20 which will come in contact with the wearer's skin are along the marginal sides of the pad. These side shields will tend to prevent the egress of urine out of the pad from the sides of the pad. Moreover, since the side shields form the marginal sides of the pad on the outer surface thereof, the side shields serve to prevent the polymeric film of the back-sheet from engaging the wearer's skin while preventing the egress of urine. As will be appreciated by those skilled in the art, the engagement of a polymeric film with skin may tend to result in irritation particularly if moisture is trapped therebetween. Since the material making up the side shields is a non-woven or fibrous material, it will exhibit a soft, cloth-like feel when it engages the wearers skin, thereby resulting in a construction which is very comfortable.

As should be appreciated from the foregoing the pad 20 of this invention is simple in construction and can be fabricated and assembled easily. In particular, the materials making up the pad's various layers can be readily shaped from sheets or webs of suitable materials. For example, the pad's back-sheet 28 can be readily die-cut from a web of moisture impervious material, e.g., a polymeric film, into a generally flat-oval shaped panel. The top-sheet 22 can be die-cut from a web of moisture pervious, non-woven material into a panel having a pair of arcuate ends with adjacent deep notches to form the double arcuate ended central section and contiguous trapezoidal shaped side sections described heretofore. The core 26 and the acquisition layer 24 can each also be die-cut from respective suitable materials. Then the various die-cut components can be assembled with suitable adhesives to complete the pad. For example, the acquisition layer and absorbent core can be interposed and adhesively secured between the central portion of the top-sheet and the back-sheet. It is then a simple matter to fold the top-sheet's trapezoidal shaped side sections around the linear marginal edges of the back-sheet, with the elastic strands undertension and a suitable adhesive interposed therebetween, to hold the elastic strands in place and form the upstanding, cloth-like exterior side shields.

Without further elaboration the foregoing will so fully illustrate our invention that others may, by applying current or future knowledge, adopt the same for use under various conditions of service.

We claim:

1. A disposable elasticized absorbent pad arranged to be worn under clothing by a person to trap and collect urine, said pad being a flexible member having an un-tensioned cup-shaped configuration and a tensioned flattened configuration having a central longitudinal axis, said member when in said un-tensioned cup-shaped configuration having upstanding marginal side portions, said pad when in said flattened configuration being of a generally flat oval shape, said pad comprising a top-sheet, a fluid acquisition layer, an absorbent core, and a back-sheet, said back-sheet being formed of a fluid impervious material and having an opposed pair of arcuate end portions and an opposed pair of linear side edges, said linear side edges of said back sheet extending parallel to said longitudinal central axis and being confined to approximately the central half of said longitudinal central axis, each of said arcuate end portions of said back-sheet terminating in an arcuate edge, said top-sheet being formed of a fluid pervious material and having an opposed pair of arcuate end portions and an opposed pair of side portions, each of said arcuate end portions of said top-sheet terminating in an arcuate edge, each of said side portions of said top-sheet being of a generally trapezoidal shape and terminating in a side edge, said arcuate end portions of said top-sheet being disposed over and secured to respective ones of said arcuate end portions of said back-sheet, said fluid acquisition layer being located over said core and under said top-sheet, said core being located over said back-sheet, each of said side portions of said top-sheet being folded along a respective fold line around a respective linear side edge of said back-sheet into engagement with said back-sheet, said fold lines extending parallel to said longitudinal central axis and being confined to approximately the central half of said longitudinal central axis, with said side edges of said side portions of said top sheet being located closely adjacent respective linear side edges of said back-sheet, said side portions of said top-sheet being adhesively secured to said back-sheet to form a pair of side shields, said side shields being elasticized and tensioned along said fold lines, whereupon said pad naturally assumes said cup-shape configuration, wherein said side shields project upward along portions of said core to form said upstanding marginal sides.

2. The disposable absorbent pad of claim 1 wherein said top-sheet is formed of a fibrous material.

3. The disposable absorbent pad of claim 1 wherein said back-sheet is formed of a polymeric film.

4. The disposable absorbent pad of claim 2 wherein said back-sheet is formed of a polymeric film.

5. The disposable absorbent pad of claim 1 additionally comprising an adhesive stripe located on said back-sheet for mounting said absorbent pad in a garment.

6. The disposable absorbent pad of claim 5 additionally comprising a release strip releasably secured over said adhesive.

7. The disposable absorbent pad of claim 1 wherein said arcuate end portions of said top-sheet and said back-sheet are of identical shape.

8. The disposable absorbent pad of claim 7 wherein said side portions of said top-sheet are each of generally trapezoidal shape and merge with the remainder of said top-sheet along respective ones of said fold lines.

9. The disposable absorbent pad of claim 8 wherein said side portions of said top-sheet are elasticized adjacent said fold lines to form said elasticized side shields.

10. The disposable absorbent pad of claim 9 wherein said top-sheet is formed of a fibrous material.

11. The disposable absorbent pad of claim 9 wherein said back-sheet is formed of a polymeric film.

12. The disposable absorbent pad of claim 10 wherein said back-sheet is formed of a polymeric film.

13. The disposable absorbent pad of claim 11 additionally comprising an adhesive stripe located on said back-sheet for mounting said absorbent pad in a garment.

14. The disposable absorbent pad of claim 13 additionally comprising a release strip releasably secured over said adhesive.

15. The disposable absorbent pad of claim 12 additionally comprising an adhesive stripe located on said back-sheet for mounting said absorbent pad in a garment.

16. The disposable absorbent pad of claim 15 additionally comprising a release strip releasably secured over said adhesive.

* * * * *

UNITED STATES PATENT AND TRADEMARK OFFICE
CERTIFICATE OF CORRECTION

PATENT NO.       : 6,440,112 B1                                      Page 1 of 1
APPLICATION NO.  : 09/472394
DATED            : August 27, 2002
INVENTOR(S)      : Frank S. Glaug and Jean A. Serafino It is certified that error appears in the above-identified patent and that said Letters Patent is hereby corrected as shown below:

On page 1 of the issued patent, the following references were omitted by the Patent Office. The references were cited in an Information Disclosure Statement filed on April 6, 2001 and considered by the Examiner on March 18, 2002.

US 3,871,378 - Grace L. Smith, et al. published March 18, 1975
US 5,092,860 - Raymond Pigneul published March 3, 1992
US 5,542,941 - Yasuko Morita published August 6, 1996

EP 0606082 - Kimberly Clark Co. published July 13, 1994

WO 93/01781 - Proctor & Gamble published February 4, 1993
WO 96/10976 - Giovanni Carlucci, et al. published April 18, 1996

Signed and Sealed this

Twentieth Day of February, 2007

JON W. DUDAS
*Director of the United States Patent and Trademark Office*